US010265496B2

(12) United States Patent
Bugamelli et al.

(10) Patent No.: US 10,265,496 B2
(45) Date of Patent: Apr. 23, 2019

(54) ANTI-ASPHYXIA VALVE ASSEMBLY

(71) Applicant: KONINKLIJKE PHILIPS N.V., Eindhoven (NL)

(72) Inventors: Antonio Bugamelli, Mars, PA (US); Duon Alex Truong, Plum Borough, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1193 days.

(21) Appl. No.: 14/401,299

(22) PCT Filed: May 16, 2013

(86) PCT No.: PCT/IB2013/053999
§ 371 (c)(1),
(2) Date: Nov. 14, 2014

(87) PCT Pub. No.: WO2013/171705
PCT Pub. Date: Nov. 21, 2013

(65) Prior Publication Data
US 2015/0136137 A1 May 21, 2015

Related U.S. Application Data

(60) Provisional application No. 61/647,582, filed on May 16, 2012.

(51) Int. Cl.
*A61M 16/00* (2006.01)
*A61M 16/20* (2006.01)
(Continued)

(52) U.S. Cl.
CPC ...... *A61M 16/206* (2014.02); *A61M 16/0066* (2013.01); *A61M 16/0622* (2014.02);
(Continued)

(58) Field of Classification Search
CPC ............ A61M 16/208; A61M 16/0816; Y10T 137/7884; F16K 15/144
(Continued)

(56) References Cited

U.S. PATENT DOCUMENTS 2,638,127 A 5/1953 Griswold
3,613,720 A * 10/1971 Welch .................. F16K 15/031
137/527
(Continued)

FOREIGN PATENT DOCUMENTS

JP 4118156 Y1 8/1966
JP 2010535085 A 11/2010
(Continued)

*Primary Examiner* — Gregory A Anderson
*Assistant Examiner* — Victoria Murphy
(74) *Attorney, Agent, or Firm* — Michael W. Haas

(57) ABSTRACT

A valve assembly (12) includes a first housing (22), a diaphragm member (24) having a plurality of individually pivotable sealing members (50), and a second housing (26) coupled to the end of the first housing over the diaphragm member. The second housing has a plurality of ports (78) spaced about the second member. The diaphragm member is structured to actuate between (i) a first state wherein the sealing members substantially seal the end of the first housing responsive to a pressure within the first housing being below a certain level, each of the ports being open in the first state, and (ii) a second state wherein the sealing members pivot away from and do not substantially seal the end of the first housing responsive to a pressure in the first housing being at or above the certain level, each sealing member substantially sealing a respective one of the ports in the second state.

9 Claims, 12 Drawing Sheets

(51) Int. Cl.
  *F16K 15/14* (2006.01)
  *A61M 16/06* (2006.01)
  *A61M 16/08* (2006.01)

(52) U.S. Cl.
  CPC .... *A61M 16/0666* (2013.01); *A61M 16/0683* (2013.01); *A61M 16/208* (2013.01); *F16K 15/144* (2013.01); *F16K 15/147* (2013.01); *A61M 16/0816* (2013.01); *Y10T 137/7884* (2015.04)

(58) Field of Classification Search
  USPC ..................................... 137/512; 604/167.03
  See application file for complete search history.

(56) References Cited

U.S. PATENT DOCUMENTS

| | | | | |
|---|---|---|---|---|
| 4,406,022 | A * | 9/1983 | Roy | A61F 2/2403 |
| | | | | 137/512 |
| 5,896,857 | A * | 4/1999 | Hely | A61M 16/208 |
| | | | | 128/203.11 |
| 8,365,731 | B2 * | 2/2013 | Ho | A61M 16/208 |
| | | | | 128/204.18 |
| 2004/0255948 | A1 | 12/2004 | Smith | |
| 2006/0076017 | A1 * | 4/2006 | Walker | A61M 16/06 |
| | | | | 128/205.24 |
| 2009/0260628 | A1 | 10/2009 | Flynn | |

FOREIGN PATENT DOCUMENTS

| | | |
|---|---|---|
| WO | WO0038772 A1 | 7/2000 |
| WO | WO2007045008 A1 | 4/2007 |

\* cited by examiner

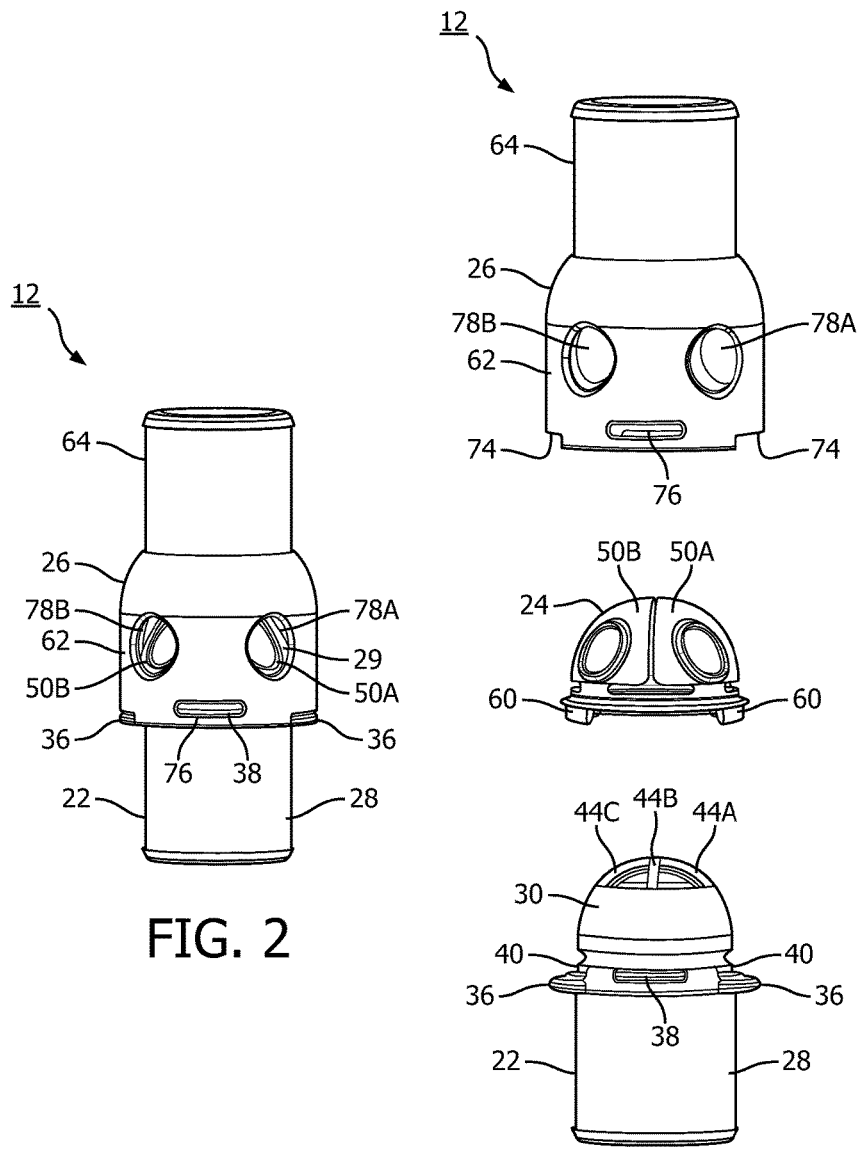

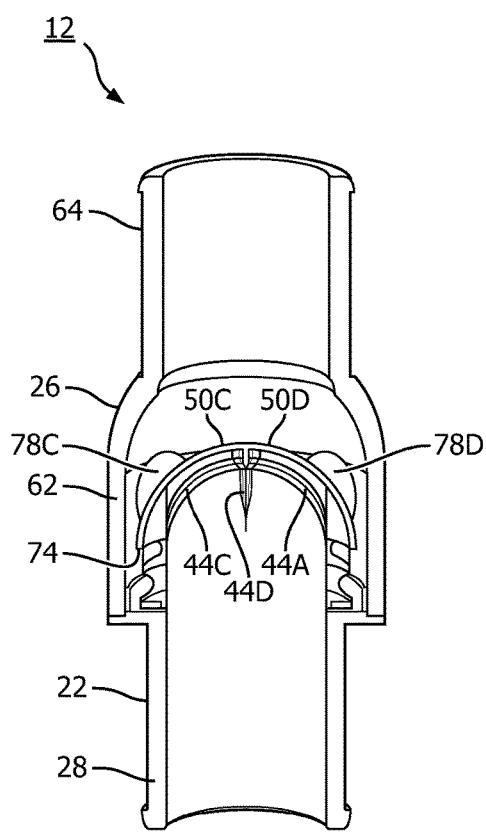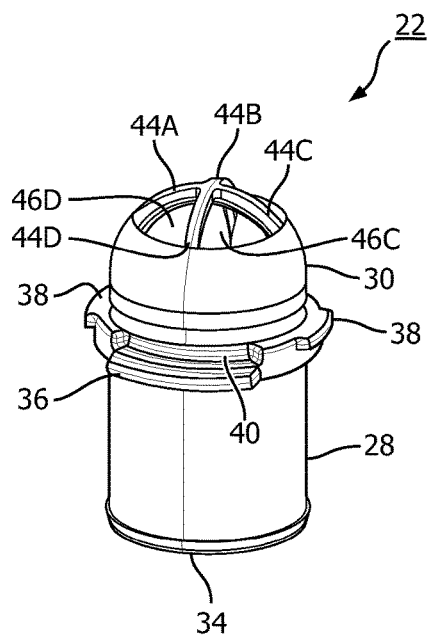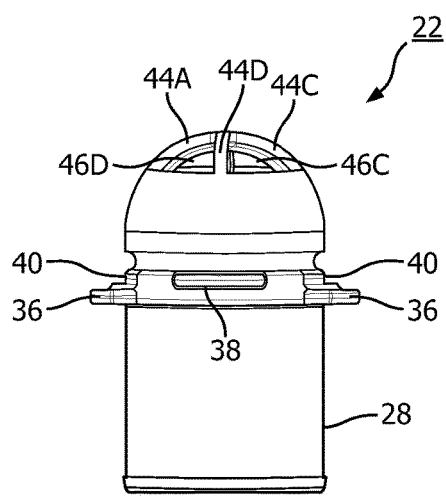
FIG. 4
FIG. 5
FIG. 6

ANTI-ASPHYXIA VALVE ASSEMBLY

CROSS-REFERENCE TO RELATED APPLICATIONS

This patent application claims the priority benefit under 35 U.S.C. § 371 of international patent application no PCT/IB2013/053999, filed May 16, 2013, which claims the priority benefit under 35 U.S.C. § 119(e) of U.S. Provisional Application No. 61/647,582 filed on May 16, 2012, the contents of which are herein incorporated by reference.

BACKGROUND OF THE INVENTION

1. Field of the Invention

The present invention pertains to a valve assembly used to control the flow of a fluid, such as, without limitation, a flow of breathing gas in a user interface device, and, in one or more particular embodiments, to an anti-asphyxia valve for use in a user interface device structured to deliver a flow of breathing gas to a user to treat a sleep disorder breathing condition such as obstructive sleep apnea (OSA).

2. Description of the Related Art

There are numerous situations where it is necessary or desirable to deliver a flow of breathing gas non-invasively to the airway of a patient, i.e., without incubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Anti-asphyxia features (AAF) used in conjunction with OSA therapy are typically required as a safety device in masks that cover the nose and mouth. During respiratory therapy, should pressure no longer become available due to a power outage or a pump failure in the ventilator or pressure support device, for example, the patient will continue to be able to breathe with the use of an AAF. Typical designs in the market place take on primarily two configurations.

The first configuration employs a flap-style valve typically positioned within the fluid coupling conduit (e.g. elbow connector) of the mask. Such a flap style valve is fundamentally a reed style check valve. As the pressure from the ventilator or pressure support device is applied, the flap style valve opens, allowing air flow to the patient while blocking an exhaust cavity on the opposite side of the flap of the flap style valve. When no pressure comes from the ventilator or pressure support device, the flap seats and allows exhalation and inhalation at atmospheric pressure through a hole to atmosphere. The flap also serves to prevent the patient from pulling air from the volume of air in the gas delivery tubes and the ventilator or pressure support device.

The second configuration employs what is commonly called a Duck-bill valve. Duck bill valves are frequently used in industrial applications where low pressure drops are required. A duck bill valve is fundamentally two symmetrically opposed reed valves (i.e., two symmetrically opposed flaps). As pressure is applied from the ventilator or pressure support device, the two flaps open in opposite directions and seal off exhaust holes provided on each side of the valve. When no pressure comes from the ventilator or pressure support device, the flaps seat with one another and allow exhalation and inhalation at atmospheric pressure through the open exhaust holes. The flap also serves to prevent the patient from pulling air from the volume of air in the gas delivery tubes and the ventilator or pressure support device.

At least two current development trends within the design of masks for non-invasive ventilation and pressure support therapies are impacting the required functionally of supporting components, such as AAF devices, used therewith. These trends are the implementation of smaller gas delivery tubing (e.g., 15 mm inside diameter) and newer, under-the-nose style mask profiles. These features require a balancing of the necessary effective flow area to limit the pressure drop across the AAF while maintaining a smaller package profile. Achieving such balancing has proven to be challenging in connection with AAFs having one of the two prior art configurations described above.

SUMMARY OF THE INVENTION

Accordingly, it is an object of the present invention to provide a valve assembly that overcomes the shortcomings of conventional valve assemblies used in, for example, user interface devices structured to deliver a flow of breathing gas to a user. This object is achieved according to one embodiment of the present invention by providing a valve assembly that balances the necessary effective flow area to limit the pressure drop across the valve assembly while maintaining a smaller package profile.

It is yet another object of the present invention to provide a method of controlling gas flow to and from a user by employing such a valve assembly.

In one embodiment, a valve assembly is provided that includes a first housing, a diaphragm member coupled to an end of the first housing, the diaphragm member having a plurality of individually pivotable sealing members, and a second housing coupled to the end of the first housing over the diaphragm member. The second housing has a plurality of ports extending though the second housing member and spaced about the second member. The diaphragm member is structured to actuate between (i) a first state wherein the sealing members substantially seal the end of the first housing responsive to a pressure within the first housing being below a certain level, each of the ports being open in the first state, and (ii) a second state wherein the sealing members pivot away from and do not substantially seal the end of the first housing responsive to a pressure within the first housing being at or above the certain level, each sealing member substantially sealing a respective one of the ports in the second state.

In another embodiment, a method is provided that employs such a valve assembly to control gas flow to and from a patient, wherein the method includes causing the diaphragm member to be in a first state wherein the sealing members substantially seal the end of the first housing responsive to a pressure within the first housing being below a certain level, each of the ports being open in the first state, allowing the patent to inhale and exhale through the ports in the first state, causing the diaphragm member to be in a second state wherein the sealing members pivot away from and do not substantially seal the end of the first housing responsive to a pressure within the first housing being at or above the certain level, each sealing member substantially sealing a respective one of the ports in the second state, and delivering a flow of breathing gas to the patient through the end of the first housing in the second state.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 2 is an isometric view, FIG. 3 is an exploded view, and FIG. 4 is a side cross-sectional view of a valve assembly according to one exemplary embodiment of the invention;

FIGS. 5-8 are isometric, side elevational, top plan and bottom plan views, respectively, of a lower housing of the valve assembly of FIGS. 2-4;

DETAILED DESCRIPTION OF EXEMPLARY EMBODIMENTS

Figure 1:
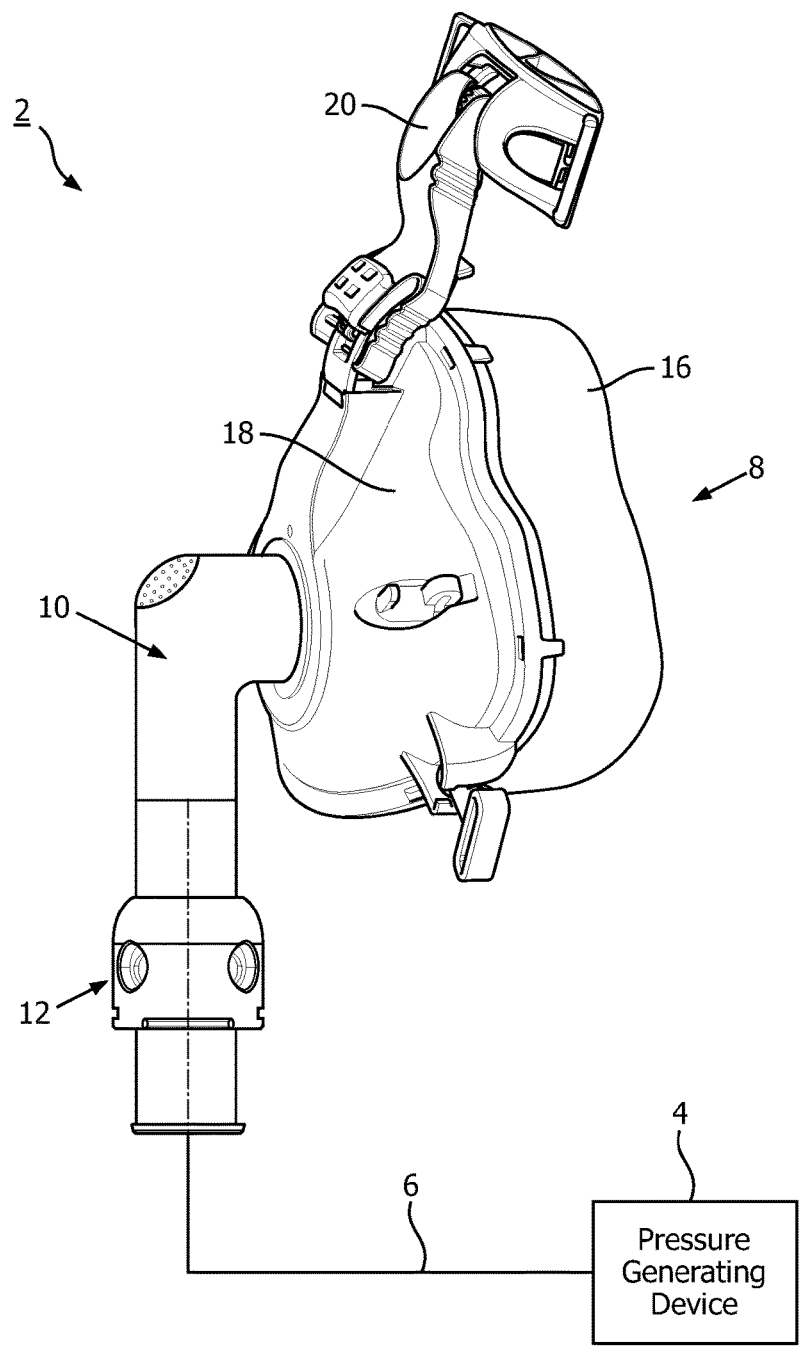
FIG. 1 is a schematic diagram of a system adapted to provide a regimen of respiratory therapy to a patient according to one exemplary embodiment of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment of the invention is generally shown in FIG. 1. System 2 includes a pressure generating device 4, a delivery conduit 6, a patient interface device 8 including an elbow conduit 10, and a valve assembly 12 (described in greater detail herein) fluidly coupled to elbow conduit 10 and delivery conduit 6. While in the illustrated embodiment, valve assembly 12 is shown as an independent assembly provided between elbow conduit 10 and delivery conduit 6, it will be understood that that is but one possible, exemplary implementation of the present invention. It will thus be appreciated that other, alternative implementations are also possible, such as, without limitation, integration of valve assembly 12 into elbow conduit 10, integration of an attachment feature which would directly mount valve assembly 12 to another portion of patient interface device 8, such as shell 18 described below, integration of valve assembly 12 directly into delivery conduit 6, or integration of valve assembly 12 directly into patient interface device 8.

Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

In the illustrated embodiment, patient interface 8 is a nasal/oral mask structured to cover the nose and mouth of the patient. However, any type of patient interface device 8, such as, without limitation, a nasal mask that covers the patient's nose, a nasal cushion having nasal prongs that are received within the patient's nares, or a full face mask that covers the patient's face, which facilitates the delivery of the flow of breathing gas to, and the removal of a flow of exhalation gas from, the airway of a patient may be used while remaining within the scope of the present invention. In the embodiment shown in FIG. 1, patient interface 8 includes a flexible cushion 16, a rigid or semi-rigid shell 18, and a forehead support 20. Straps (not shown) of a headgear component may be attached to shell 18 and forehead support 20 to secure patient interface device 8 to the patient's head. An opening in shell 18 to which elbow conduit 10 is coupled allows the flow of breathing gas from pressure generating device 4 to be communicated to an interior space defined by shell 18 and cushion 16, and then, to the airway of a patient. The opening in shell 18 also allows the flow of exhalation gas (from the airway of such a patient) to be communicated to valve assembly 12 as described herein.

FIG. 2 is an isometric view, FIG. 3 is an exploded view, and FIG. 4 is a side cross-sectional view of valve assembly 12 according to one exemplary embodiment. Valve assembly 12 includes a lower housing 22, a diaphragm member 24 coupled to lower housing 22, and an upper housing 26 also coupled to lower housing 22 over top of diaphragm member 24. Each of these components is described in greater detail below.

FIGS. 5-8 are isometric, side elevational, top plan and bottom plan views, respectively, of lower housing 22. In the exemplary embodiment, lower housing 22 is made from a rigid or semi-rigid material, such as a polycarbonate or an injection molded thermoplastic. Lower housing 22 includes a lower portion 28 and an upper portion 30.

Lower portion 28 has a cylindrical shape and includes a lower inner chamber 32 (FIG. 8) that defines a gas flow path along the longitudinal axis of the inner chamber 32. A first end 34 of lower portion 28 is structured to be fluidly coupled to delivery conduit 6 (FIG. 1). Lower portion 28 further includes first tabs 36, second tabs 38 and recesses 40 spaced about the outer perimeter of lower portion 28. The function of each of these parts is described elsewhere herein.

Figure 7:
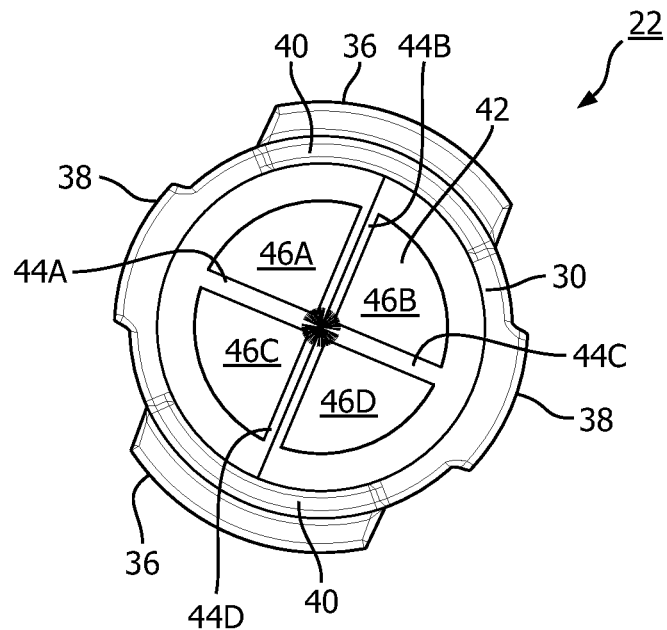
Figure 8:
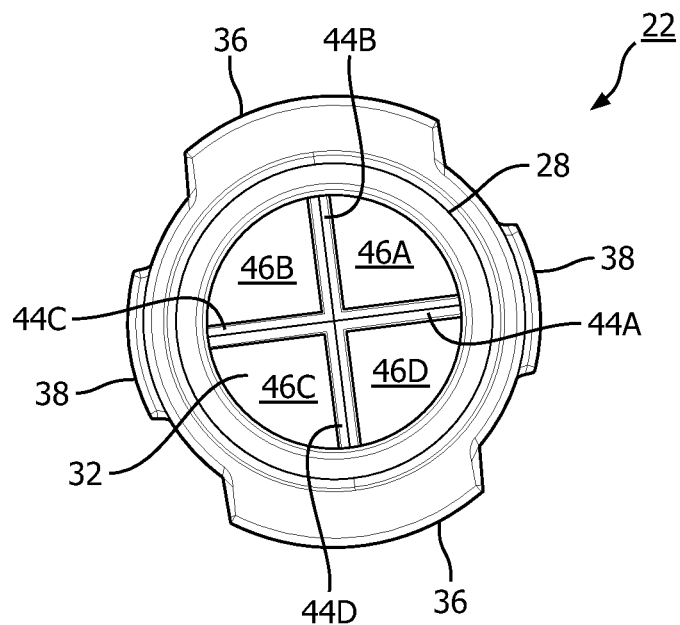

Upper portion 30 has a domed, half sphere shape and defines an upper inner chamber 42 (FIG. 7). In addition, upper portion 30 includes four rib members 44A-44D (providing a crossing structure) which together define four pie shaped openings 46A-46D in the top end of upper portion 30.

Figure 9:
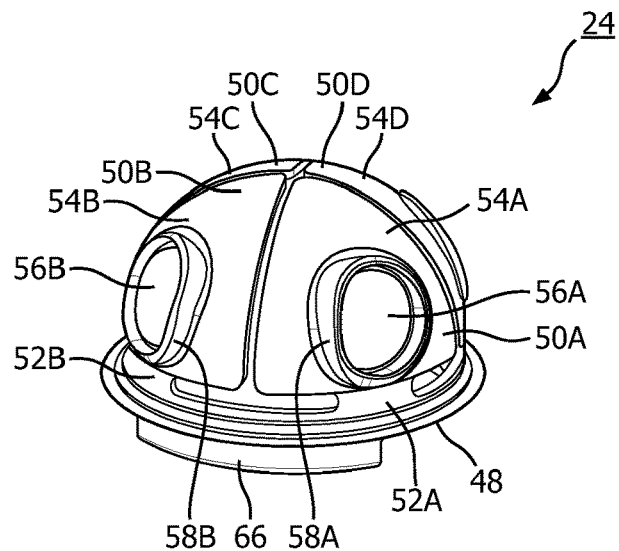
FIGS. 9-11 are isometric, top plan and side elevational views, respectively, of a diaphragm member of the valve assembly of FIGS. 2-4.
Figure 10:
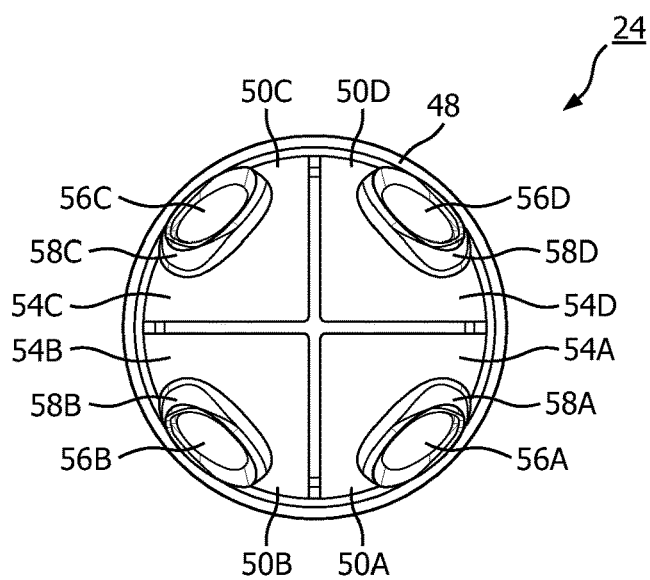
Figure 11:
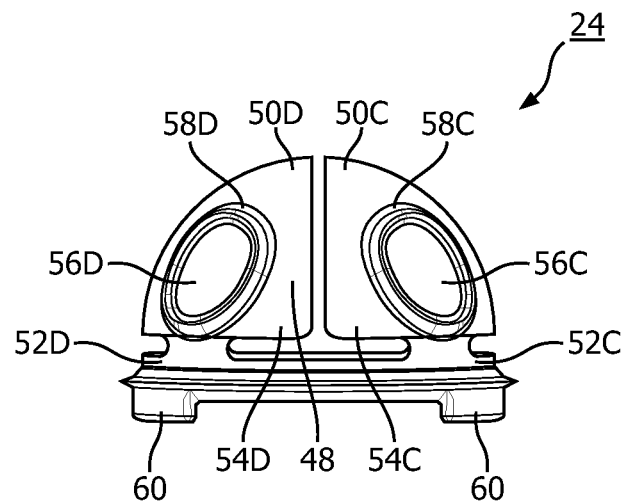

FIGS. 9-11 are isometric, top plan and side elevational views, respectively, of diaphragm member 24 according to the exemplary embodiment. As seen in FIGS. 9-11, in the exemplary, non-limiting embodiment, diaphragm member 24 has a domed, half sphere shape. In addition, in the exemplary embodiment, diaphragm member 24 is made of an elastomeric material, such as, without limitation, silicone, urethane, natural rubber, latex, and/or fabrics and has a durometer in the range of 3 Shore A to 70 Shore A or equivalent. Diaphragm member 24 includes a circular base portion 48. A plurality of petal-like sealing members 50 extend upwardly from base portion 48. In the illustrated embodiment, four sealing members 50 (labeled 50A-50D) are provided as part of diaphragm member 24. It will be understood, however, that that is meant to be exemplary only, and that more or less than four sealing members 50 may also be provided.

Each sealing member 50A-50D includes an attachment portion 52A-52D that is coupled to base portion 48, and a sealing body portion MA-MD coupled to attachment portion 52A-52D. In the exemplary embodiment, each sealing body portion MA-MD generally has a pie shape. In addition, each sealing body portion MA-MD has a projecting member 56A-56D extending from the top side thereof. The projecting members 56A-56D each have an outer perimeter defined by an outer wall 58A-58D. In addition, projecting members 56A-56D have a first shape (i.e., cross-sectional shape) that matches a second shape of ports (described elsewhere herein) that are provided in upper housing 26. In the illustrated, non-limiting embodiment, the projecting members 56A-56D are hollow extensions and have a generally circular cross-sectional shape.

Sealing body portion MA-MD of each sealing member 50A-50D is structured to pivot on the associated attachment portion 52A-52D toward and away from a central axis of diaphragm member 24 through base portion 48. The significance of this feature is explained elsewhere herein.

Diaphragm member 24 further includes a number of tab members 60 extending downwardly from base portion 48. As described in more detail elsewhere herein, tab members 60 are used to couple diaphragm member 24 or lower housing 22.

Figure 12:
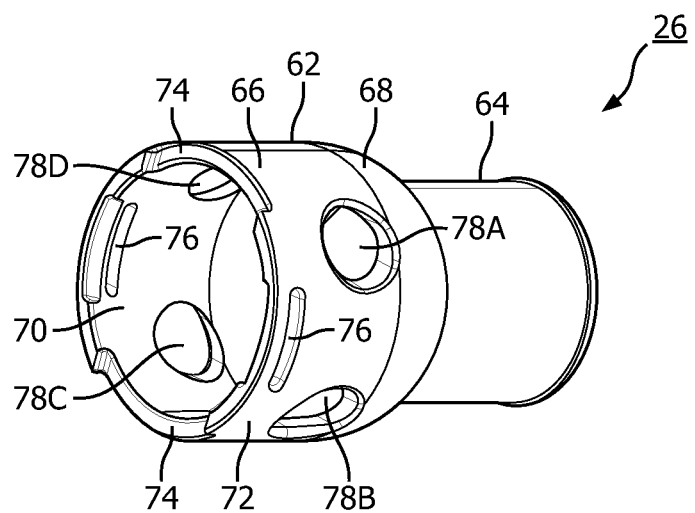
FIGS. 12 and 13 are isometric and side elevational views, respectively, of an upper housing of the valve assembly of FIGS. 2-4.
Figure 13:
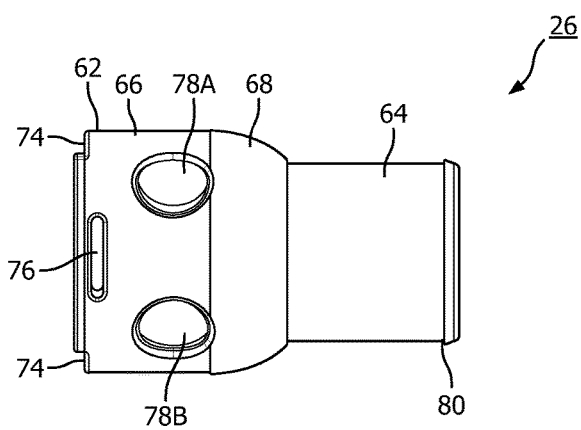

FIGS. 12 and 13 are isometric and side elevational views, respectively, of upper housing 26 according to the exemplary embodiment. In the exemplary embodiment, upper housing 26 is made from a rigid or semi-rigid material, such as a polycarbonate or an injection molded thermoplastic. Upper housing 26 includes a lower portion 62 and an upper portion 64.

In the exemplary embodiment, lower portion 62 has a cylindrically shaped bottom section 66 and a hemispherically shaped top section 68, and upper portion 64 has a cylindrical shape. Together, lower portion 62 and upper portion 64 include an inner chamber 70 (FIG. 12) that defines a gas flow path along the longitudinal axis of the inner chamber 70 (aligned with the gas flow path along inner chamber 32 described elsewhere herein). A first end 72 of upper housing 26 is structured to be fluidly coupled to lower housing 22, and lower portion 62 includes recesses 74 and slots 76 spaced about the outer perimeter of lower portion 62 to facilitate the connection between upper housing 26 and lower housing 22 as described elsewhere herein.

When valve assembly 12 is assembled (as described herein), top section 68 is structured to provide an appropriate amount of offset area to diaphragm member 24 to allow for movement of sealing members 50A-50D as described in detail below. In the exemplary embodiment, the gap between top section 68 and diaphragm member 24 is set such that there is enough effective flow area around diaphragm member 24 and top section 68 to allow the controlling air flow restriction to atmosphere to be through ports 78 (described below). If this gap were larger, it would mean more movement of sealing members 50A-50D, which may not be feasible at the required minimum treatment pressures. If the gap were smaller, there would be a higher restriction, which would lead to higher air rush noise from the valve assembly 12 or the inability to achieve exhalation/inhalation thresholds.

Furthermore, lower portion 62 includes a plurality of ports 78 spaced about the outer periphery of lower portion 72. Each port 78 extends completely through lower portion 62. In the illustrated embodiment, four ports 78 (labeled 78A-78D) are provided in lower portion 62. It will be understood, however, that that is meant to be exemplary only, and that more or less than four ports 78 may also be provided. However, it will also be understood that the number of ports 78 will equal the number of sealing members 50 provided as part of diaphragm member 24. In addition, as noted elsewhere herein, the shape of ports 78 will match the shape of projecting member 56. Thus, in the exemplary embodiment, each of ports 78A-78D has a generally circular shape (although other shapes are possible, such as, without limitation, oblong, rectangular or triangular shapes).

In the exemplary embodiment, second end 80 of upper housing 26 is structured to be fluidly coupled to elbow conduit 10 (FIG. 1).

Valve assembly 12 is assembled in the following manner. First, diaphragm member 24 is coupled to upper portion 30 of lower housing 22 in a manner wherein each tab member 60 of diaphragm member 24 is received within a respective recess 40 of lower housing 22. When this is done, sealing member 50A will be seated against rib members 44A and 44B, sealing member 50B will be seated against rib members 44B and 44C, sealing member 50C will be seated against rib members 44C and 44D, and sealing member 50D will be seated against rib members 44D and 44A. As a result, in this state, sealing member 50A will cover opening 46A of lower housing 22, sealing member 50B will cover opening 46B of lower housing 22, sealing member 50C will cover opening 46C of lower housing 22, and sealing member 50D will cover opening 46D of lower housing 22, thus substantially sealing that end of lower housing 22. As used herein, the term "substantially sealing" shall mean that 25% or less of a fluid flow will be able to pass through the seal.

In one exemplary embodiment, the flow through valve assembly 12 is optimized with the minimization of the width of rib members 44A-44D as well as with the addition of sharp edges parallel with the flow path. This maximizes the effective flow area through valve assembly 12 through openings 46A-46D. In addition, a reduced pressure drop from a larger effective flow area lowers the air velocity at the same flow point and thus reduces the opportunity for noise through valve assembly 12. Furthermore, the movement of sealing members 50A-50D significantly out of the flow path at lower pressures maximizes the effective flow area through valve assembly 12 through upper portion 64. At higher pressures/flows through valve assembly 12, the minimized flow intrusion of sealing members 50A-50D reduces the opportunity for noise within valve assembly 12.

Next, upper housing 26 is coupled to lower housing 22 over top of diaphragm member 24. In particular, lower portion 62 of upper housing 26 is coupled to upper portion 30 of lower housing 22 by positioning each of the first tabs 36 of lower housing 22 in a respective recess 74 of upper housing 26 and causing each of the second tabs 38 of lower housing 22 to be received within a respective slot 76 of upper housing 26 (FIGS. 2 and 4). When this is done, diaphragm member 24 will be received within lower portion 62 of upper housing 26 in a manner wherein sealing member 50A is located immediately adjacent port 78A, sealing member 50B is located immediately adjacent port 78B, sealing member 50C is located immediately adjacent port 78C, and sealing member 50D is located immediately adjacent port 78D.

The connection of upper housing 26 to lower housing 22 in the manner just described is one wherein those two parts can be selectively coupled to and decoupled from one another. As will be appreciated, this allows for selective access to diaphragm member 24 so that it can be serviced and/or replaced as needed. Assembly of upper housing 26 to lower housing 22 may also employ any of a number of alternative retention methods/mechanisms (integrated into upper housing 26 to lower housing 22) that allow for service and/or replacement of diaphragm member 24, such as, without limitation, living plastic hinges, deflecting arms, threading, interference fit components, and an additional retention ring. In a further alternative, assembly of upper housing 26 to lower housing 22 may also be such that access to diaphragm member 24 so that it can be serviced and/or replaced as needed is not provided. Such as assembly would require a mechanism integrated into upper housing 26 and/or lower housing 22 that would not allow the user to separate those components, and may include, for example and without limitation, ultrasonically welding upper housing 26 to lower housing 22, chemical bonding upper housing 26 to lower housing 22, snap fit features, deflecting arms without retraction features, and locking threads.

Figure 14:
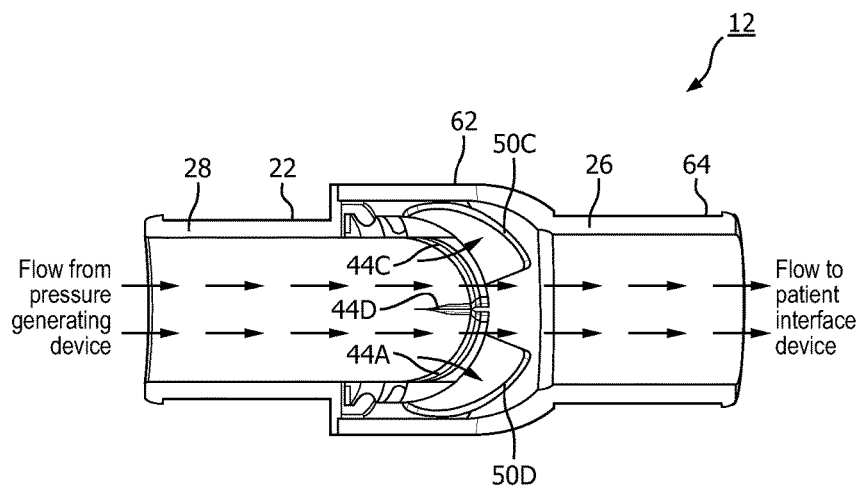
FIGS. 14-16 are cross-sectional views illustrating the operation of the valve assembly of FIGS. 2-4.

In operation, during therapy, when the gas flow generated by pressure generating device 4 and delivered to valve assembly 12 though delivery conduit 6 exceeds some minimum value (e.g., 4 cm $H_2O$), each sealing member 50A-50D will be caused to pivot on the associated attachment portion 52A-52D away from the central axis of base portion 48 and toward the inner walls of lower portion 62 of upper housing 26, thereby uncovering/unsealing the openings 46A-46D in the top end of upper portion 30 as shown in FIG. 14. In addition, when sealing members 50A-50D pivot completely in this manner, each projecting member 56A-56D will be received within and sealingly engage a corresponding one of the ports 78A-78D. As a result, the gas delivered from pressure generating device 4 and received by valve assembly 12 will follow the flow path indicated by the arrows in FIG. 14 and will be delivered to patient interface device 8. In addition, that gas flow will be prevented from escaping to atmosphere through ports 78A-78D because they are substantially sealed by sealing members 50A-50D.

Figure 15:
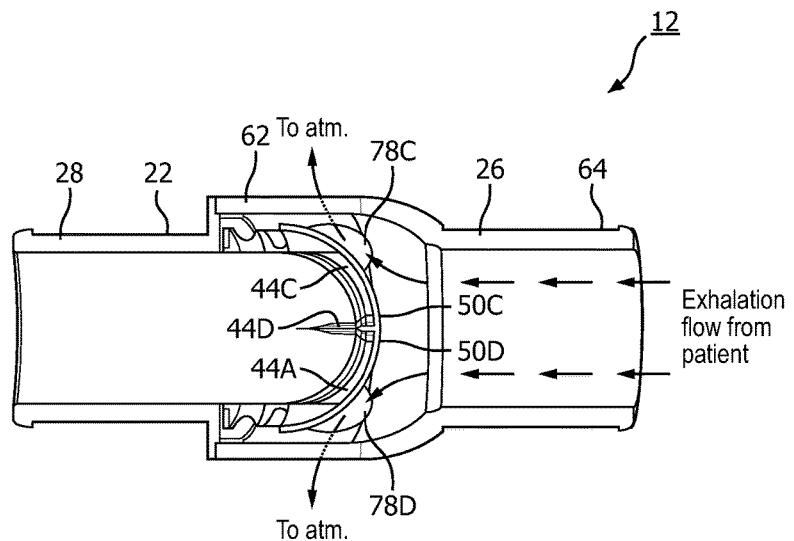
Figure 16:
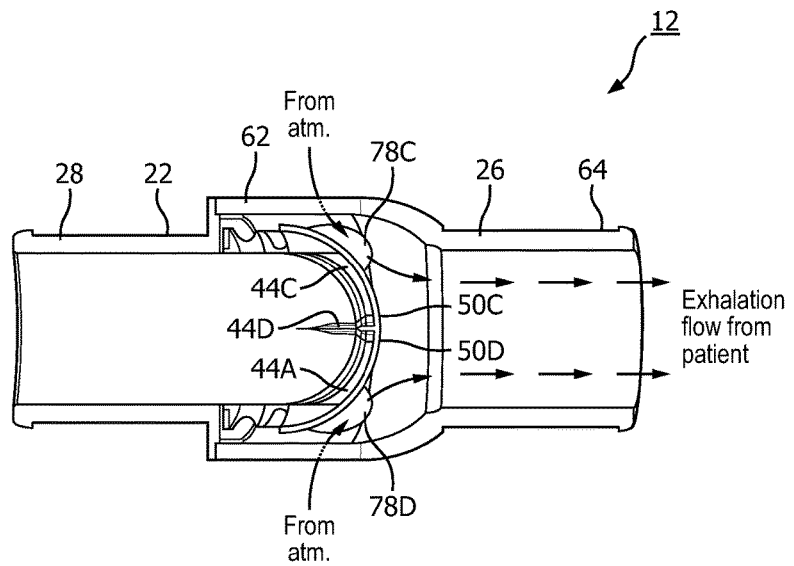

Thereafter, when the gas flow generated by pressure generating device 4 and delivered to valve assembly 12 though delivery conduit 6 falls below the minimum value (e.g., 4 cm $H_2O$), each sealing member 50A-50D will be caused to pivot on the associated attachment portion 52A-52D back toward the openings 46A-46D in the top end of upper portion 30 to a position wherein they cover and substantially seal the openings 46A-46D in the manner described elsewhere herein (i.e., by engaging the rib members 44A-44D). This state is shown in FIGS. 15 and 16, and, due to the shape of diaphragm member 24 and sealing members 50A-50D, will be achieved regardless of the current orientation of valve assembly 12. In this state, ports 78A-78D are no longer sealed and thus the interior of upper housing 26 is open to atmosphere. As a result, two things are possible: (i) patient exhalation gasses from patient interface device 8 may be vented to atmosphere through ports 78A-78D (FIG. 15), and (ii) the patient may inhale through patient interface device 8, drawing inhalation gasses from atmosphere through ports 78A-78D (FIG. 16). In addition, in this state, the patient will be prevented from trying to breathe the "dead" volume of air in delivery conduit 6 and pressure generating device 4.

As described elsewhere herein, in the illustrated, exemplary embodiment, four ports 78A-78D equally spaced about the outer perimeter of upper housing 62 are provided. This design allow for continued air flow through valve assembly 12 should a portion of it come to rest against a person's body or bedding. Designs containing only one port or two equally spaced ports run the risk of being blocked if certain orientations of the device contact bedding or the person's body. As will be appreciated, the benefit just described may be enjoyed in alternative exemplary embodiments wherein the number of equally spaced ports 78 is three or five or more. In such alternative configurations, the number of sealing members 50 that is provided will match the number of ports 78.

Figure 17:
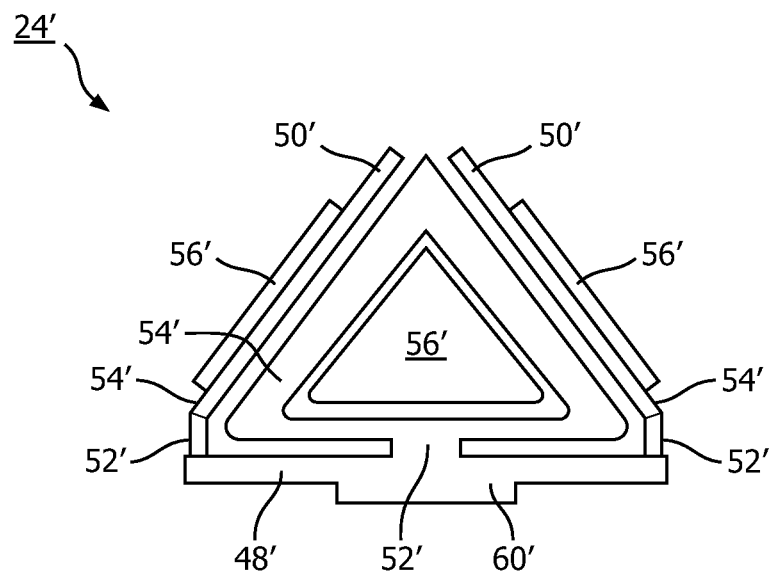
FIG. 17 is a side elevational view of a diaphragm member according to an alternative exemplary embodiment of the invention.

FIG. 17 is a side elevational view of a diaphragm member 24' according to an alternative exemplary embodiment. As seen in FIG. 17, in this embodiment, diaphragm member 24' is shaped like a pyramid, and is structured to be used with an alternative lower housing and an alternative upper housing each having a shape that is complimentary to the shape of diaphragm member 24'. Like diaphragm member 24, diaphragm member 24' is made of an elastomeric material, such as, without limitation, silicone, urethane, natural rubber, latex, and/or fabrics, and may have the durometer ranges specified elsewhere herein. Diaphragm member 24' includes a square base portion 48'. A plurality of petal-like sealing members 50' extend upwardly from base portion 48'. In the illustrated embodiment, four sealing members 50' are provided as part of diaphragm member 24', although more or less (e.g., three) may also be used. Each sealing member 50' includes an attachment portion 52' that is coupled to base portion 48', and a sealing body portion 54' coupled to attachment portion 52'. In the exemplary embodiment, each sealing body portion 54' has a generally triangular shape. In addition, each sealing body portion 54' has a projecting member 56' extending from the top side thereof. The projecting members 56' each have an outer perimeter defined by an outer wall. In addition, projecting members 56' have a first shape (i.e., cross-sectional shape) that matches a second shape of ports (described elsewhere herein) that are provided in the upper housing that is to be used with diaphragm member 24'. In the illustrated, non-limiting embodiment, the projecting members 56' are hollow extensions and have a generally triangular cross-sectional shape. Diaphragm member 24' further includes a number of tab members 60' extending downwardly from base portion 48' which are used for attachment as described elsewhere herein.

Figure 18:
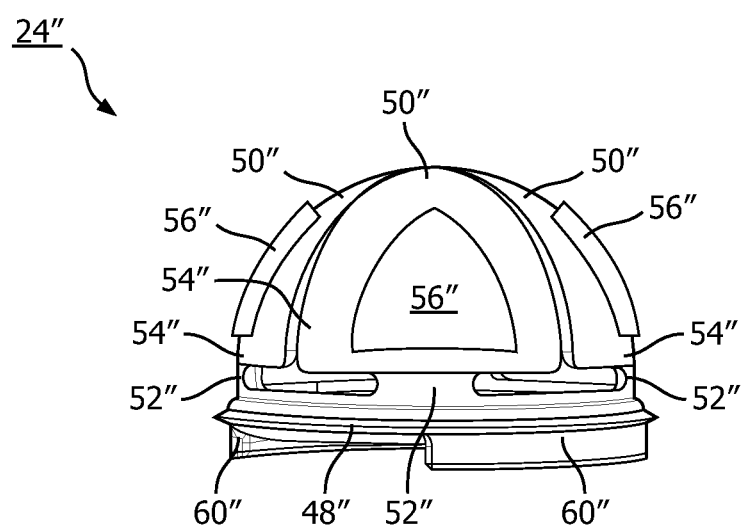
FIG. 18 is a side elevational view of a diaphragm member according to another alternative exemplary embodiment of the invention.

FIG. 18 is a side elevational view of a diaphragm member 24'' according to another alternative exemplary embodiment. As seen in FIG. 18, in this embodiment, diaphragm member 24''' has a domed, half sphere shape, and thus may be used with lower housing 22 and upper housing 26. Diaphragm member 24'' includes a circular base portion 48''. A plurality of petal-like sealing members 50'' extend upwardly from base portion 48''. In the illustrated embodiment, four sealing members 50'' are provided as part of diaphragm member 24'', although more or less may also be used. Each sealing member 50'' includes an attachment portion 52'' that is coupled to base portion 48'', and a sealing body portion 54'' coupled to attachment portion 52''. In the exemplary embodiment, each sealing body portion 54'' has a pie shape. In addition, each sealing body portion 54'' has a solid projecting member 56'' extending from the top side thereof. The projecting members 56'' each have an outer perimeter defined by an outer wall. In addition, projecting members 56'' have a first shape (i.e., cross-sectional shape) that matches a second shape of ports 78 described elsewhere herein. Diaphragm member 24'' further includes a number of tab members 60'' extending downwardly from base portion 48'' which are used for attachment as described elsewhere herein. In addition, in the present embodiment, base portion 48'', attachment portions 52'', sealing body portions 54'' and tab members 60'' are made of a flexible elastomeric material, such as, without limitation, silicone, urethane, natural rubber, latex, and/or fabrics, and have a durometer in the range of 3 Shore A to 70 Shore A or equivalent, and projecting member 56'' are made of a rigid or semi-rigid material, such as, without limitation, thermoplastics, silicone, urethane, natural rubber, latex, and/or fabrics, and have a durometer that is greater than the durometer of base portion 48'', attachment portions 52'', sealing body portions 54'' and tab members 60'', for example in the range of 10 Shore A to 100 Shore A or equivalent.

Figure 19:
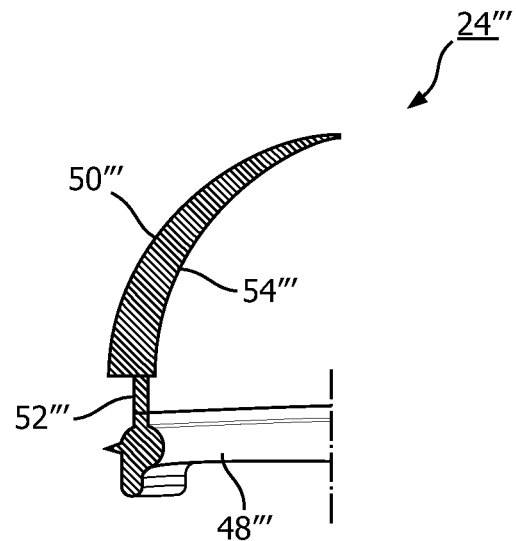
FIG. 19 is a cross-sectional view of a diaphragm member according to still another alternative exemplary embodiment of the invention.

FIG. 19 is a side cross-section view of a portion of a diaphragm member 24'' according to still another alternative exemplary embodiment. As seen in FIG. 19, in this embodiment, diaphragm member 24'' includes a plurality of petal-like sealing members 50''' which extend upwardly from base portion 48'' (attached via an attachment portion 52''), wherein the sealing body portion 54''' of each sealing members 50''' has a cross-sectional thickness that varies. In particular, in sealing members 50''', the cross-sectional thickness of the sealing body portion 54''' is greatest at the proximal end thereof nearest base portion 48'', and least at the distal end thereof. In one particular embodiment, a ratio of the greatest cross-sectional thickness to the least cross-sectional thickness is 10 to 1, or, alternatively 5 to 1 or 2 to 1.

Figure 20:
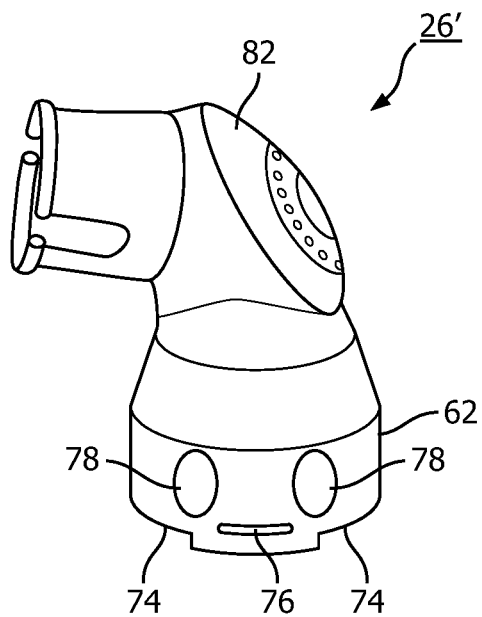
FIG. 20 is an isometric view of an upper housing according to an alternative exemplary embodiment of the invention that may be used in place of the upper housing of FIGS. 12 and 13.

FIG. 20 is an isometric view of an upper housing 26' according to an alternative exemplary embodiment of the present invention. Upper housing 26' is structured to be used with lower housing 22 and diaphragm member 24, 24'', or 24''' as described elsewhere herein, and an thus includes a lower portion 62 as described elsewhere herein. In addition, upper housing 26' includes an elbow connector portion 82 in place of upper portion 64. Elbow connector portion 82 is structured to be directly connected to shell 18 (FIG. 1).

Figure 21:
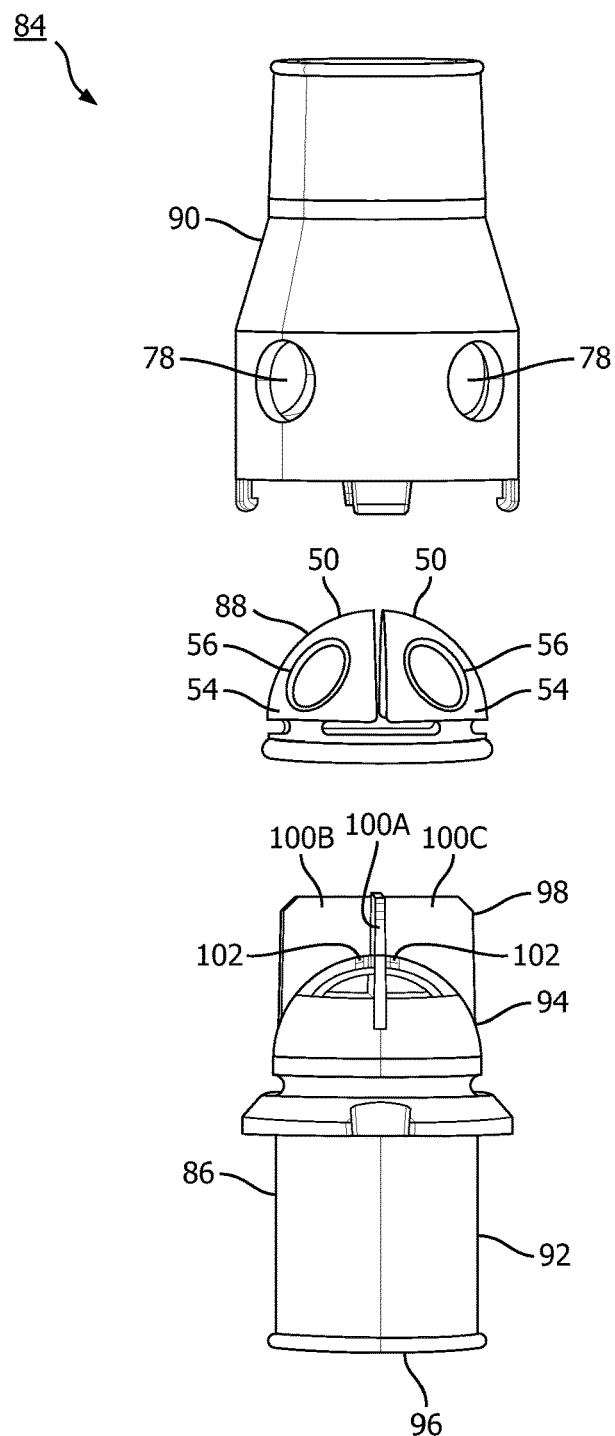
FIG. 21 is an exploded view of a valve assembly according to an alternative exemplary embodiment of the invention.

FIG. 21 is an exploded view of a valve assembly 84 according to an alternative exemplary embodiment of the present invention which, except as described below, is similar to valve assembly 12. Valve assembly 84 includes a lower housing 86, a diaphragm member 88 structured to be coupled to lower housing 86, and an upper housing 90 structured to be coupled to lower housing 86 over top of diaphragm member 88. Lower housing 86 of the present embodiment is described in detail below. Diaphragm member 88 is similar to diaphragm member 24, and includes sealing members 50 having sealing body portions 54 and projecting members 56 as described elsewhere herein. Upper housing 90 is similar to upper housing 26 and includes ports 78 as described elsewhere herein.

Figure 22:
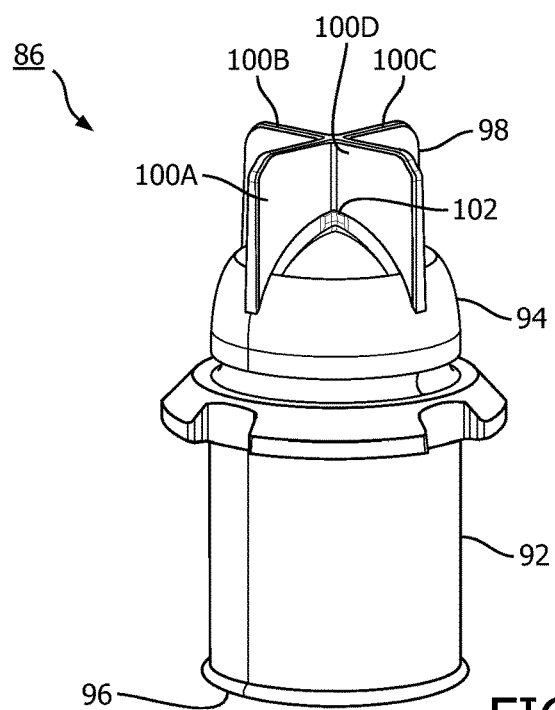
FIG. 22 is an isometric view of a lower housing of the valve assembly of FIG. 21.

FIG. 22 is an isometric view of lower housing 86. Lower housing 86 is made from a rigid or semi-rigid material, such as a polycarbonate or an injection molded thermoplastic. Lower housing 86 includes a lower portion 92 and an upper portion 94. Lower portion 92 has a cylindrical shape and includes a lower inner chamber that defines a gas flow path along the longitudinal axis of lower housing 86. A first end 96 of lower portion 92 is structured to be fluidly coupled to delivery conduit 6 (FIG. 1). Upper portion 94 has a domed, half sphere shaped portion structured to receive diaphragm member 88. In addition, lower housing 86 includes a finned member 98 that is provided at a top end of upper portion 94 and that is structured to be received within upper housing 90.

Figure 23:
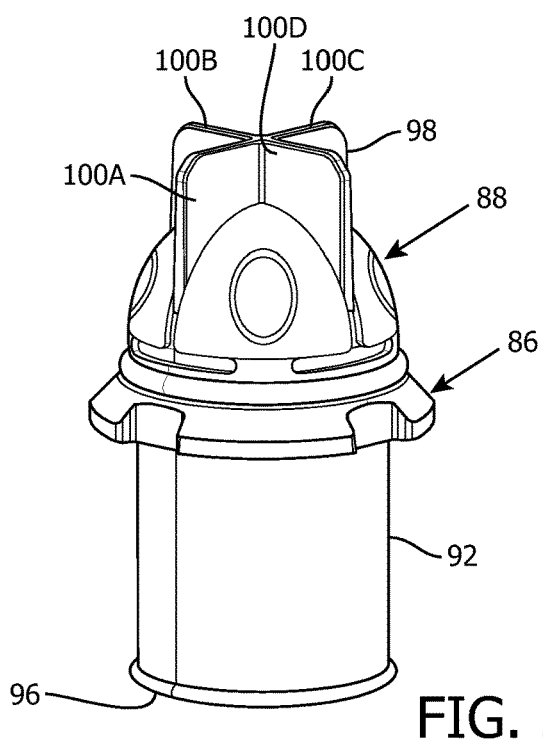
FIG. 23 is an isometric view showing a diaphragm member and the lower housing of the valve assembly of FIG. 21.

Finned member 98 includes four rib members 100A-100D which, when valve assembly 84 is assembled, define four separate gas flow paths within upper housing 90, with each flow path being associated with a respective one of the sealing members 50 of the diaphragm member 88. As shown in FIG. 23, when diaphragm member 88 is coupled to lower housing 86, each rib member 100A-100D is received in a space in between an adjacent pair of sealing members 50. Finned member 98 thus provides flow/pressure separation within valve assembly 84. In addition, finned member 98 also includes four seat members 102 (positioned at the intersection points of rib members 100A-100D) structured to provide a seating engagement surface for the associated sealing member 50 to close off the associated gas flow path when the gas flow generated by pressure generating device 4 is less than the minimum value required to open the diaphragm member 88.

Moreover, other variations of the diaphragm member 24 are possible that will change the flow performance and operating characteristics and that may be beneficial to the proposed and alternate uses of valve assembly 12. For example, a localized mass could be added to sealing members 50 or 50' (even located off-center) to impart a different performance characteristic to the assembly (e.g., to change the center of mass). For instance, if addition silicone was applied to the distal tips sealing members 50 or 50', it would take more flow force/pressure to force the sealing members 50 or 50' off the valve seat and out of the flow path. As another example, fabrics, thin sheets of thermoplastic, or even wax paper could be used as an alternate material for sealing members 50 or 50'. As still another example, living plastic hinge could be an alternative for connecting the sealing members 50 or 50' to the lower housing. As still another example, if the upper housing 26 were ultrasonically welded to the lower housing 28, there could be an opportunity to eliminate the elastomeric ring around the whole assembly and replace it with four individual set sealing members. Finally, rib members 44 may have rounded edges instead of sharp edges, or may need to change to accommodate alternatively shaped sealing members (e.g., take an oblong profile).

While the present invention has been described in connection with a patient interface device used to treat, for example, OSA, it will be understood that that is meant to be exemplary, and that the principles of the present invention can be can also be applied in connection with other face masks applications where concern for asphyxia may occur, such as, without limitation, anesthesia delivery masks or general use face masks where users may be unable to manipulate a mask to maintain breathing. Furthermore, as the valve assembly embodiments described herein actuate upon very basic fluid dynamic principles, they may also be used in industrial applications, for example, and without limitation, as a combination check valve/bleed-off valve where air circulation may require access to atmosphere if direct system pressure is not applied. The target industrial applications would be smaller and low pressure air control systems like HVAC, furnace air control, or automotive relief systems.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A valve assembly, comprising:
a first housing;
a diaphragm member coupled to an end of the first housing, the diaphragm member having sealing members configured to be individually pivotable, each sealing member of the sealing members having a projecting member protruding away from a surface of the sealing member and from the end of the first housing; and
a second housing coupled to the end of the first housing over the diaphragm member, the second housing having ports extending through the second housing and spaced about the second housing,
wherein the diaphragm member is structured to actuate between a first state and a second state,
wherein, responsive to a pressure within the first housing being below a certain level, the diaphragm member is caused to be in the first state in which (i) the sealing members seal the end of the first housing and (ii) the ports are open, and wherein, responsive to the pressure within the first housing being at or above the certain level, the diaphragm member is caused to be in the second state in which (i) the projecting members seal the ports and (ii) the end of the first housing is open,
wherein the diaphragm member has a base portion coupled to the end of the first housing,
wherein the sealing members extend from and are pivotable relative to the base portion,
wherein each sealing member of the sealing members includes a sealing body portion and the projecting member extending from a top side of the sealing body portion,
wherein a shape of each of the projecting members matches a shape of each of the ports,
wherein in the second state each of the projecting members is received within a respective one of the ports to seal the port, and,
wherein the base portion and each sealing body portion of each sealing member of the sealing members are made of an elastomeric material having a first durometer and wherein the projecting member of each sealing member of the sealing members is made of rigid or semi-rigid material having a second durometer that is greater than the first durometer.

2. The valve assembly according to claim 1, wherein the sealing members comprise three or more sealing members, and wherein the ports comprise three or more ports.

3. The valve assembly according to claim 1, wherein the diaphragm member comprises a dome-shaped structure, wherein the projecting members protrude from the dome-shaped structure.

4. The valve assembly according to claim 1, wherein the diaphragm member comprises a pyramid-shaped structure, wherein the first housing comprises a structural shape complimentary to the diaphragm member's structural shape.

5. The valve assembly according to claim 1, wherein the first durometer of the elastomeric material of the base portion and each sealing body portion of each sealing member of the sealing members, and the second durometer of the elastomeric material of the projecting member of each sealing member of the sealing members are in the range of 3 Shore A to 70 Shore A.

6. The valve assembly according to claim 1, wherein a cross-sectional thickness of each sealing body portion varies from a proximal end thereof nearest the base portion to a distal end thereof opposite the proximal end.

7. The valve assembly according to claim 6, wherein the cross-sectional thickness is greatest at the proximal end and least at the distal end.

8. A valve assembly, comprising:
a first housing;
a diaphragm member coupled to an end of the first housing, the diaphragm member having sealing members configured to be individually pivotable, each sealing member of the sealing members having a projecting member protruding away from a surface of the sealing member and from the end of the first housing; and
a second housing coupled to the end of the first housing over the diaphragm member, the second housing having ports extending through the second housing and spaced about the second housing,
wherein the diaphragm member is structured to actuate between a first state and a second state,
wherein, responsive to a pressure within the first housing being below a certain level, the diaphragm member is caused to be in the first state in which (i) the sealing members seal the end of the first housing and (ii) the ports are open, and wherein, responsive to the pressure within the first housing being at or above the certain level, the diaphragm member is caused to be in the second state in which (i) the projecting members seal the ports and (ii) the end of the first housing is open,
wherein the end of the first housing includes a plurality of rib members defining orifices, and
wherein in the first state each sealing member of the sealing members engages at least one of the rib members to seal each of the orifices.

9. A valve assembly, comprising:
a first housing;
a diaphragm member coupled to an end of the first housing, the diaphragm member having sealing members configured to be individually pivotable, each sealing member of the sealing members having a projecting member protruding away from a surface of the sealing member and from the end of the first housing; and
a second housing coupled to the end of the first housing over the diaphragm member, the second housing having ports extending through the second housing and spaced about the second housing,
wherein the diaphragm member is structured to actuate between a first state and a second state,
wherein, responsive to a pressure within the first housing being below a certain level, the diaphragm member is caused to be in the first state in which (i) the sealing members seal the end of the first housing and (ii) the ports are open, and wherein, responsive to the pressure within the first housing being at or above the certain level, the diaphragm member is caused to be in the second state in which (i) the projecting members seal the ports and (ii) the end of the first housing is open, and
wherein the end of the first housing includes a finned member protruding away from the end of the first housing and defining gas flow paths within the second housing, each gas flow path of the gas flow paths being associated with a respective one of the sealing members.

* * * * *